United States Patent

Kowalski et al.

[11] Patent Number: 5,922,937
[45] Date of Patent: Jul. 13, 1999

[54] INDIVIDUAL COMPONENT HEADFORM IMPACT TEST DRIVE

[75] Inventors: Edward Kowalski, Rochester Hills; Gerald S. Locke, Lake Orion; Tom Russell, Bloomfield Hills; Ted Konieczny, Warren, all of Mich.

[73] Assignee: Lear Corporation, Southfield, Mich.

[21] Appl. No.: 08/920,514

[22] Filed: Aug. 29, 1997

[51] Int. Cl.⁶ .................................................. G01M 7/00
[52] U.S. Cl. ........................................ 73/12.14; 73/12.13
[58] Field of Search ............................... 73/12.01, 12.06, 73/12.09, 12.12, 12.13, 12.14

[56] References Cited

U.S. PATENT DOCUMENTS

| 974,450 | 11/1910 | Tully | 73/12.12 |
| 5,046,352 | 9/1991 | Kingery et al. | 73/12.06 |
| 5,285,687 | 2/1994 | Ringel et al. | 73/12.14 |

FOREIGN PATENT DOCUMENTS

| 462100 | 2/1975 | U.S.S.R. | 73/12.14 |
| 1522068 | 11/1989 | U.S.S.R. | 73/12.14 |

*Primary Examiner*—Max H. Noori
*Attorney, Agent, or Firm*—Brooks & Kushman P.C.

[57] ABSTRACT

A head-impact test device is used for crash-testing individual vehicle components, and includes a support structure with a pendulum member pivotally connected to the support structure. The pendulum member includes an end portion. A dummy headform is releasably connected to the end portion of the pendulum member, and includes a metal base portion. An electromagnet is disposed within the end portion of the pendulum member for selectively securing the metal base portion of the dummy headform to the end portion. A component stand is positioned adjacent the support structure for supporting a component to be tested. The electromagnet is operative to release the headform for impact against the component after the headform has been accelerated by the pendulum member.

15 Claims, 3 Drawing Sheets

INDIVIDUAL COMPONENT HEADFORM IMPACT TEST DRIVE

TECHNICAL FIELD

The present invention relates to a head-impact test device, and more particularly to a headform impact test device for testing individual vehicle interior components outside of a vehicle environment.

BACKGROUND OF THE INVENTION

Federal Motor Vehicle Safety Standards require head-impact testing of various vehicle interior components, such as headliners, A-pillar trim cover components, steering wheel, etc. Such components are typically tested within a fully assembled motor vehicle. Usually, a firing structure is set up within the vehicle for firing a headform directly at an interior component to be tested. The headform includes a plurality of accelerometers therein for testing deceleration as the headform engages the particular component being tested. Accordingly, energy dissipation characteristics of the particular component may be tested by monitoring the accelerometers in the headform.

A typical prior art firing structure-type test device is a free motion headform test device, such as a FMVSS 201-U test machine manufactured by MGA Research Corporation of Burlington, Wis. or a FMH test system manufactured by MTS Systems Corporation of Eden Prairie, Minn. A common problem with such firing structures is that it is difficult to repeatably and accurately control firing velocity and direction of the headform for testing and it is expensive to acquire the vehicle bodies in quantities necessary for the development of head impact countermeasures. This lack of repeatability may adversely affect test results.

This type of component testing is highly expensive and inconvenient for design purposes because the headform firing structure is typically employed within a fully assembled vehicle. Accordingly, entire vehicles must be used for such testing, and it is difficult to acquire the vehicle bodies in quantities necessary to perfect energy dissipation characteristics of a particular component being tested. A head impact test typically deforms the body sheet metal changing the characteristics of the structure underlying the component under test.

Accordingly, it is desirable to provide a head-impact test device for crash-testing individual vehicle components which does not require testing within an assembled vehicle. It is desirable to provide such a test device in which individual components may be tested separately, and appropriate data may be gathered for component energy dissipation performance testing.

DISCLOSURE OF THE INVENTION

As a result of Lear Corporation's continuing efforts to improve vehicle safety, the present invention provides a head-impact test device for crash-testing individual vehicle components which utilizes a large pendulum structure for accelerating and releasing a dummy headform for impact against a test component for testing component energy dissipation characteristics.

More specifically, the present invention provides a head-impact test device for crash-testing individual vehicle components, which includes a support structure and a pendulum member pivotally connected to the support structure. The pendulum member includes an end portion with a dummy headform releasably connected to the end portion. The dummy headform includes a metal base portion. An electromagnet is disposed within the end portion of the pendulum member for selectively securing the base portion of the dummy headform to the end portion. A component stand is provided for supporting a component to be tested. The electromagnet is operative to release the headform for impact against the component after the headform has been accelerated to the desired velocity by the pendulum member. Pendulum height and gravity determine the velocity.

In a preferred embodiment, a decelerator is positioned beneath the pendulum member and includes a hydraulic damper system for engaging the end portion of the pendulum member for stopping pivotal movement of the pendulum member. A rotational variable displacement transducer (RVDT) is positioned at the pivotal connection between the pendulum member and the support structure for sensing rotational position of the pendulum.

Accordingly, an object of the present invention is to provide a head-impact test device for testing individual vehicle components which is configured to test the individual components separately from the vehicle.

Another object of the present invention is to provide a head-impact test device for crash-testing individual vehicle components wherein velocity of the dummy headform is accurate and repeatable.

A further object is to eliminate the need for full vehicle bodies for the development of head impact countermeasures.

The above objects and other objects, features, and advantages of the present invention are readily apparent from the following detailed description of the best mode for carrying out the invention when taken in connection with the accompanying drawings.

DETAILED DESCRIPTION OF THE PREFERRED EMBODIMENTS

Figure 1:
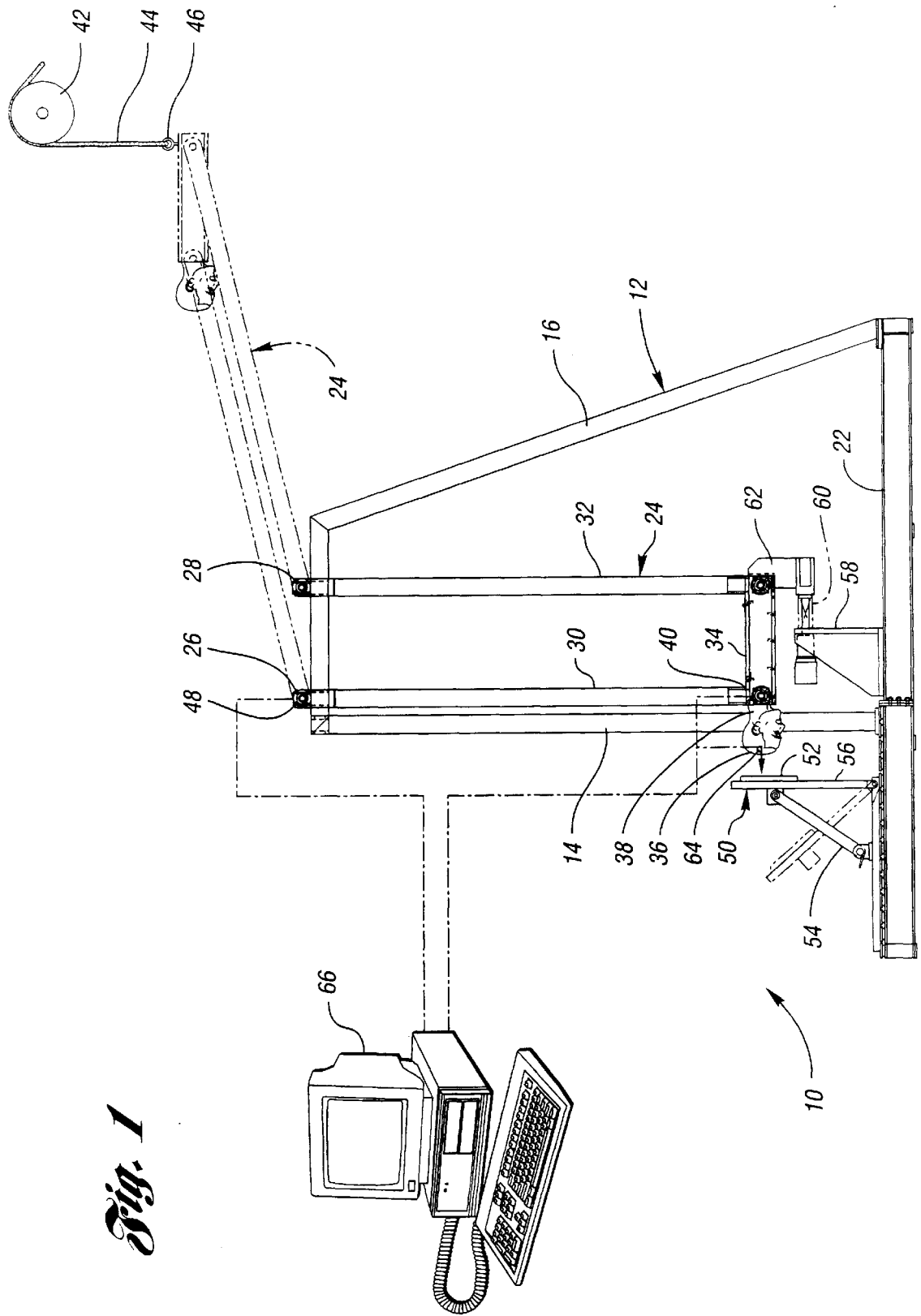
FIG. 1 is a schematically arranged side view of a headform impact test device assembly in accordance with the present invention.
Figure 2:
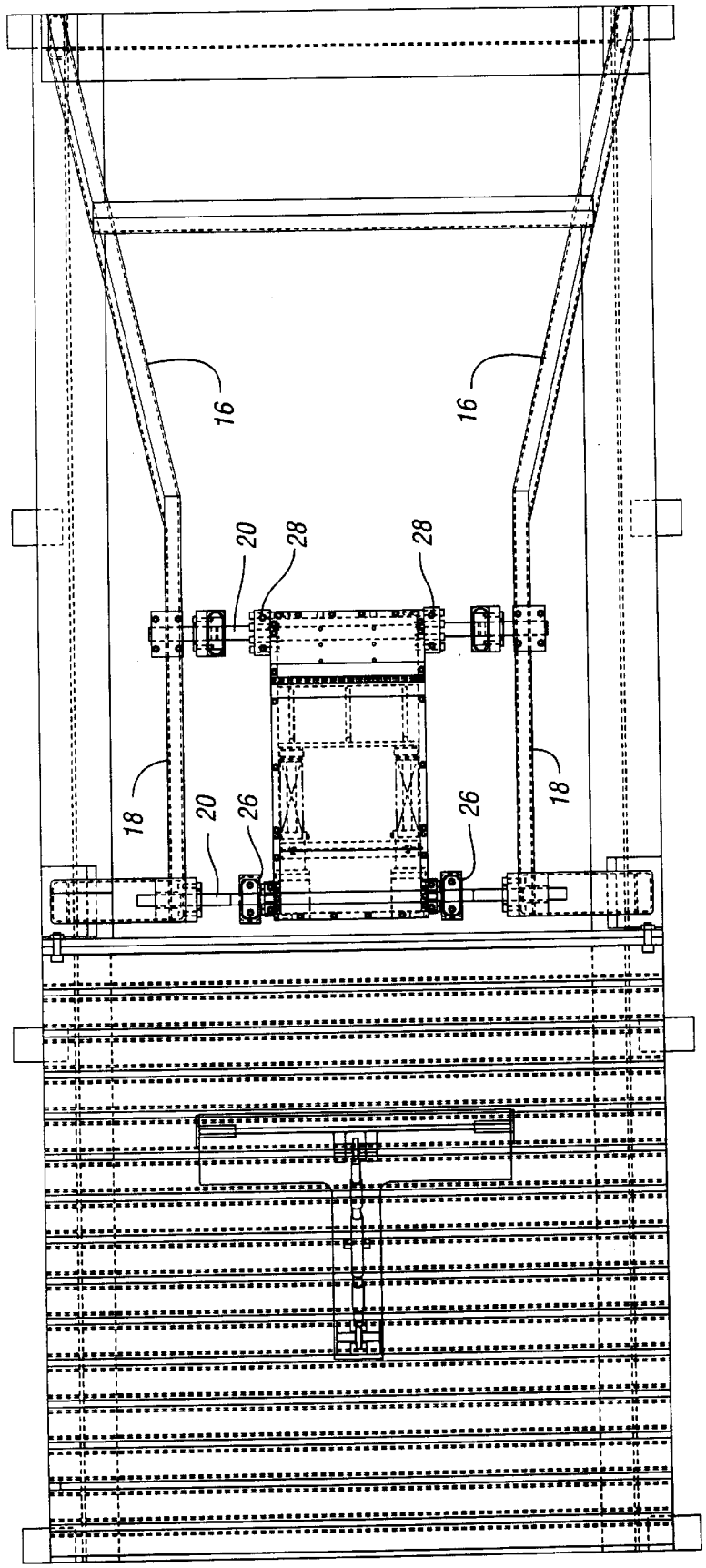
FIG. 2 is a top plan view of the test device assembly shown in FIG. 1.
Figure 3:
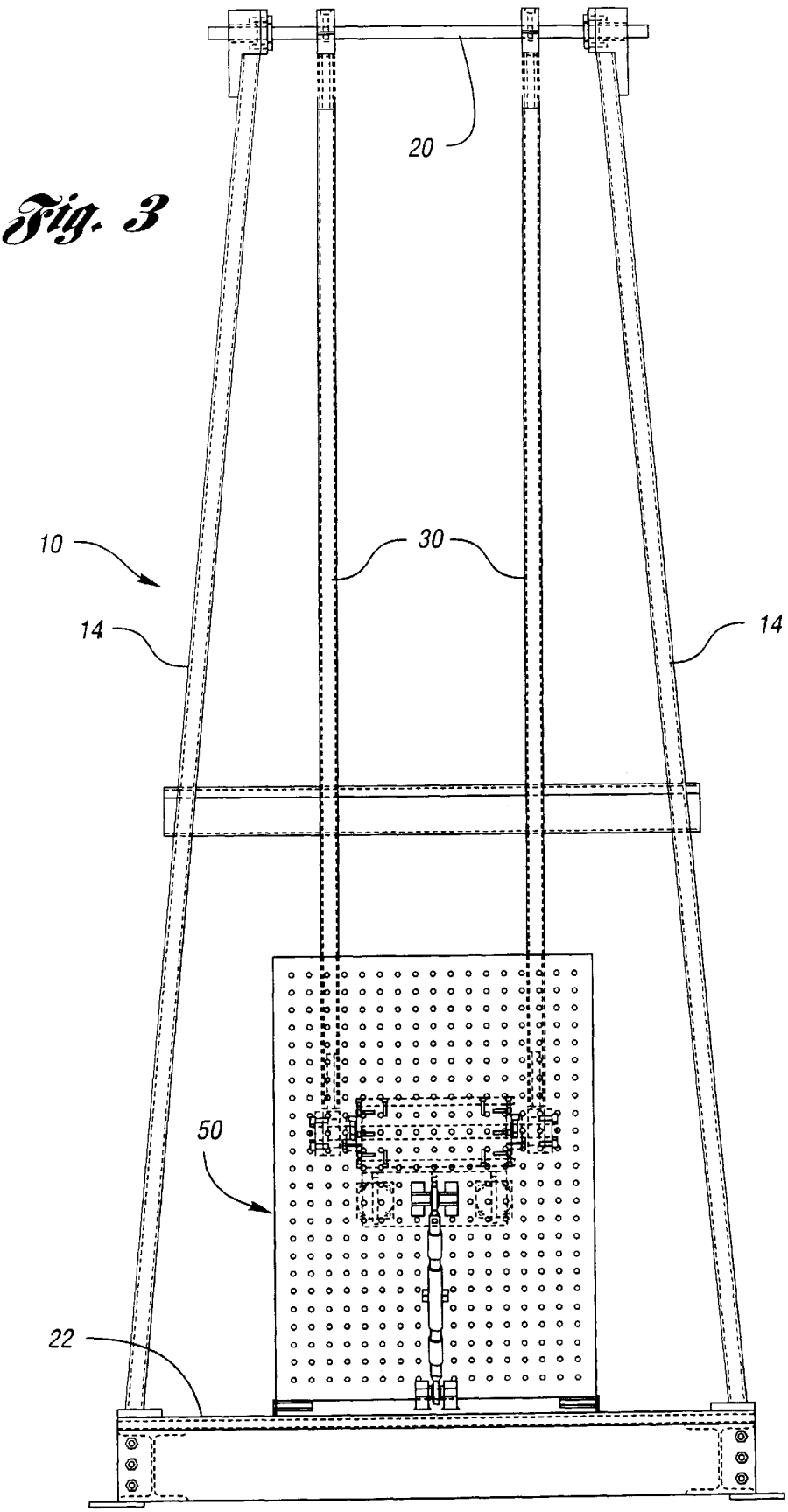
FIG. 3 is an end view of the test device assembly shown in FIG. 1.

Referring to FIGS. 1–3, a head impact test device 10 is shown in accordance with the present invention for crash testing individual vehicle components. The head impact test device 10 includes a support bar structure 12, including vertical bars 14,16 and horizontal bars 18,20. The support bar structure 12 is supported on top of a base structure 22.

A pendulum structure 24 is pivotably connected to the horizontal bars 20 at the pivot joints 26,28. The pendulum structure 24 includes parallel support bars 30,32 having an end portion 34 connected thereto.

A dummy headform 36 is releasably connected to the end portion 34 of the pendulum structure 24 as shown in FIG. 1. The dummy headform includes a metal base portion 38. The dummy headform is a federally prescribed test component as described in 49 C.F.R. §572 (L) - (free motion headform). The headform 36 shown in FIG. 1 is schematically arranged for illustrative purposes only, and not exactly representative of the federally prescribed headform.

An electromagnet 40 is disposed within the end portion 34 of the pendulum structure 24 for selectively securing the metal base portion 38 of the dummy headform 36 or a laser component target alignment device to the end portion 34. The preferred electromagnet 40 is a 12 volt d.c. small rectangular electromagnet such as model EM711 from Magnetool of Southfield, Mich. The electromagnet 40 includes a control box connected to the support structure with a release button for manual adjustment of the headform position or removal of the laser targeting device.

A pendulum 42 is provided with a cord 44 for releasable attachment to a pneumatic release mechanism 46 on the end portion 34 of the pendulum structure 24 for pivoting the pendulum structure 24 to the raised position shown in phantom in FIG. 1 prior to release for acceleration.

A rotational variable displacement transducer (RVDT) 48 is positioned at the pivot joint 26 for sensing rotational position of the pendulum structure 24 prior to release for adjusting the end portion 34 of the pendulum structure 24 to the appropriate height for headform speed control. The preferred RVDT is a Model No. 06030003, Serial No. G96 transducer from Trans-Tek of Ellington, Conn.

A component stand 50 is positioned adjacent the support structure 12 for supporting a component 52 to be tested. The component stand 50 preferably includes appropriate support bars 54 for supporting the face plate 56 of the component stand 50. Preferably, the component stand 50 is of substantially sound structural integrity. The component stand 50 may be universally indexed angularly, laterally, longitudinally and vertically.

A decelerator 58 is positioned beneath the pendulum member 24 and is supported upon the base 22. The decelerator 58 includes a hydraulic damper 60 for engaging the bracket 62 which extends downwardly from the end portion 34 of the pendulum structure 24. The stopper 58 must be sturdily mounted to stop the 500 pound swing weight of the pendulum structure.

The dummy headform 36 includes a plurality of accelerometers 64 disposed therein for sensing acceleration and/or deceleration of the dummy headform in various directions.

A computer 66 is electrically interconnected with the headform accelerometers for gathering data.

Accordingly, in order to test a particular individual vehicle component using the present invention, the component 52 is secured against the face plate 56 of the component stand 50, and the headform 36 is secured to the end portion 34 of the pendulum member 24 by energizing the electromagnet 40 to attract the metal base portion 38 of the dummy headform 36. The hoist and pulley 42 is then actuated to rotate the pendulum structure 24 to the raised position shown in phantom in FIG. 1. The raised position of the pendulum structure 24 may be selectively adjusted according to the readout of the RVDT 48 for accurately controlling velocity of the headform 36. The pneumatic release mechanism 46 then releases the end portion 34 of the pendulum structure 24 to allow acceleration of the dummy headform 36 toward the component 52.

Just prior to the engagement of the bracket 62 with the hydraulic damper 60, the electromagnet 40 is de-energized to release the metal base portion 38 of the dummy headform 36 to allow the dummy headform 36 to travel toward, and impact against, the component 52 to be tested. Once the dummy headform 36 has been released by the electromagnet 40, the bracket 62 engages against the damper 60 for stopping pivotal movement of the pendulum structure 24. The dummy headform 36 then impacts against the component 52 for test purposes. Appropriate acceleration and deceleration data may then be gathered from the accelerometer 64 within the headform 36 for testing energy dissipation characteristics of the component 52.

Analog circuitry is used for monitoring raised height of the pendulum structure 24, and for actuating de-energization of the electromagnet 40 for release of the headform 36. Appropriate software may be provided in the computer 66 for accomplishing Federal Motor Vehicle Safety Standard testing requirements.

A velocity pick-up light trap may also be employed for fiber optically monitoring pendulum velocity. Also, data acquisition and high speed video may be triggered by the velocity pick-up.

Any variety of different test components 52 could be secured to the component stand 50 for such testing. No limitation thereof is considered.

In an alternative embodiment, the RVDT 48 is replaced with a digital rotary encoder for measuring angular position and angular velocity of the pendulum structure. Because the rotary encoder is digital, programmability of the encoder allows substantial accuracy in headform release by the electromagnet. Also, raising of the pendulum structure by means of the hoist and pulley 42 can be digitally controlled for velocity accuracy and repeatability. The preferred encoder is a Model No. HR62510000100 from Danaher Controls of Gurnee, Ill.

The velocity pick-up device and accelerometers 64 provide analog outputs which go through a signal conditioner to an analog/digital converter. The rotary encoder also outputs to the A/D converter. The signal conditioning system is preferably a standard system available from Kinetic Systems Corporation, and the A/D converter is preferably a Microstar Laboratories System. The A/D card is preferably a Model No. DAP3000A, and the Quad Decoder card is preferably a Model No. MSXB-023. The A/D convertor communicates with a CPU for controlling and monitoring the various components.

A temperature and humidity sensor may also be provided adjacent the test stand for providing a digital output which may logged on a strip chart-type recorder and monitored by the CPU.

While the best mode for carrying out the invention has been described in detail, those familiar with the art to which this invention relates will recognize various alternative designs and embodiments for practicing the invention within the scope of the appended claims.

What is claimed is:

1. A head-impact test device for crash-testing individual vehicle components, comprising:

a support structure;

a parallelogram-type pendulum member pivotally connected to the support structure, and having an end portion;

a dummy headform releasably connected to the end portion of the parallelogram-type pendulum member such that the dummy headform maintains a predetermined orientation regardless of the pivotal position of the pendulum member when the headform is attached to the end portion to thereby avoid imparting angular momentum on the headform when the headform is released from the end portion, the dummy headform including a metal base portion;

an electromagnet disposed within the end portion of the pendulum member for selectively securing the metal base portion of the dummy headform to the end portion; and a component stand positioned adjacent the support structure for supporting a component to be tested;

wherein the electromagnet is operative to release the headform for impact against the component after the headform has been accelerated by the pendulum member.

2. The head-impact test device of claim 1, further comprising a decelerator positioned beneath the pendulum member and including a hydraulic damper for engaging the end portion of the pendulum member for stopping pivotal movement of the pendulum member.

3. The head-impact test device of claim 1, further comprising a rotational variable displacement transducer (RVDT) positioned at the pivotal connection between the pendulum member and the support structure for sensing angular position of the pendulum.

4. The head-impact test device of claim 1, wherein said dummy headform includes a plurality of accelerometers disposed therein.

5. The head-impact test device of claim 2, wherein said end portion includes a bracket extending downwardly therefrom for engagement with the hydraulic damper.

6. The head-impact test device of claim 2, further comprising a pulley operative to raise the end portion of the pendulum.

7. A head-impact test device for crash-testing individual vehicle components, comprising:

a support structure;

a parallelogram-type pendulum member pivotally connected to the support structure, and having an end portion;

a dummy headform releasably connected to the end portion of the parallelogram-type pendulum member such that the dummy headform maintains a predetermined orientation regardless of the pivotal position of the pendulum member when the headform is attached to the end portion to thereby avoid imparting angular momentum on the headform when the headform is released from the end portion, dummy headform including a metal base portion;

an electromagnet disposed within the end portion of the pendulum member for selectively securing the metal base portion of the dummy headform to the end portion;

a component stand for supporting a component to be tested; and a decelerator positioned beneath the pendulum member and including a hydraulic damp for engaging the end portion of the pendulum member for stopping pivotal movement of the pendulum member;

wherein the electromagnet is operative to release the headform for impact against the component after the headform has been accelerated by the pendulum member.

8. The head-impact test device of claim 7, further comprising a rotational variable displacement transducer (RVDT) positioned at the pivotal connection between the pendulum member and the support structure for sensing rotational displacement of the pendulum.

9. The head-impact test device of claim 7, wherein said dummy headform includes a plurality of accelerometers disposed therein.

10. The head-impact test device of claim 7, wherein said end portion includes a bracket extending downwardly therefrom for engagement with the hydraulic damper.

11. The head-impact test device of claim 7, further comprising a pulley and release mechanism operative to raise and release the end portion of the pendulum.

12. A head-impart test device for crash-testing individual vehicle components, comprising:

a support structure;

a parallelogram-type pendulum member pivotally connected to the support structures, and having an end portion;

a dummy headform releasably connected to the end portion of the parallelogram-type pendulum member such that the dummy headform maintains a predetermined orientation regardless of the pivotal position of the pendulum member when the headform is attached to the end portion to thereby avoid imparting angular momentum on the headform when the headform is released from the end portion, the dummy headform including a metal base portion;

an electromagnet disposed within the end portion of the pendulum member for selectively securing the metal base portion of the dummy headform to the end portion;

a component stand for supporting a component to be tested;

a decelerator positioned beneath the pendulum member and including a hydraulic damper for engaging the end portion of the pendulum member for stopping pivotal movement of the pendulum member;

a rotational variable displacement transducer (RVDT) positioned at the pivotal connection between the pendulum member and the support structure for sensing rotational displacement of the pendulum; and wherein the electromagnet is operative to release the headform for impact against the component after the headform has been accelerated by the pendulum member.

13. The head-impact test device of claim 12, wherein said dummy headform includes a plurality of accelerometers disposed therein.

14. The head-impact test device of claim 12, wherein said end portion includes a bracket extending downwardly therefrom for engagement with the hydraulic damper.

15. The head-impact test device of claim 12, further comprising a pulley operative to raise the end portion of the pendulum.

* * * * *